(12) United States Patent
Hardy et al.

(10) Patent No.: US 6,344,739 B1
(45) Date of Patent: Feb. 5, 2002

(54) EDDY CURRENT PROBE WITH MULTI-USE COILS AND COMPACT CONFIGURATION

(75) Inventors: Florian Hardy, St-Augustin de Desmaures; Rock Samson, St-Nicolas, both of (CA)

(73) Assignee: R/D Tech Inc., Quebec (CA)

( * ) Notice: Subject to any disclaimer, the term of this patent is extended or adjusted under 35 U.S.C. 154(b) by 0 days.

(21) Appl. No.: 09/350,183

(22) Filed: Jul. 9, 1999

(30) Foreign Application Priority Data

Feb. 12, 1999 (JP) .......................................... 11-034446
Feb. 12, 1999 (JP) .......................................... 11-034504
Feb. 12, 1999 (JP) .......................................... 11-034580

(51) Int. Cl.$^7$ .......................... G01N 27/90; G01R 33/12
(52) U.S. Cl. ...................................... 324/220; 324/242
(58) Field of Search ................................ 324/220, 228, 324/234, 236, 237, 238, 239, 240, 241, 242, 243, 260

(56) References Cited

U.S. PATENT DOCUMENTS

| 3,693,415 A | 9/1972 | Whittington ................. 73/67.9 |
| 4,741,878 A | 5/1988 | Gebelin et al. ............. 376/248 |

(List continued on next page.)

FOREIGN PATENT DOCUMENTS

| EP | 0248726 | 12/1987 |
| EP | 0 368 580 A2 | 5/1990 |
| EP | 0 392 859 A2 | 10/1990 |
| EP | 0848815 | 3/1997 |
| GB | 2 269 673 A | 2/1994 |
| JP | 05133941 | 5/1993 |
| JP | 6160357 | 6/1994 |
| JP | 08189919 | 7/1996 |
| JP | 9119919 | 5/1997 |
| JP | 11108902 | 4/1999 |
| WO | WO90 02920 A1 | 3/1990 |

OTHER PUBLICATIONS

Babcock & Wilcox, Chapter 55 "Service, Life Extension and Enhancements", pp. 55–1 to 55–13.
Babcock & Wilcox, Chapter 50, "Nuclear Steam Supply Systems and Safety", pp. 50–1–to 50–17.
Nuson Inspection Services, "Flexible Ultrasonic Probed for Tubing", pp. 1 and 2.
Nuson, "Ultrasonic Measurement Techniques For Heat Exchanger Tubing", pp. 1 to 6.
Nuson's Research & Development, "Improvement of the Large Range Diameter Probe", pp. 1 and 2.
17$^{th}$. EPRI Steam Genetaror NDE Workshop, Aug. 17–19, 1998, Breckenridge, Colorado, USA, "Evaluation of Currently Applied Ultrasonic Sizing Techniques For Stress Corrosion Cracks in Steam Generator Tubes", prepared by René Krutzen et al. Nuson Inspection Services, Amsterdam, the Netherlands, pp. 1 to 13.

Primary Examiner—Safet Metjahic
Assistant Examiner—Reena Aurora
(74) Attorney, Agent, or Firm—swabey ogilvy renault

(57) ABSTRACT

In an eddy current testing probe, efficiency is improved by multiplexing, at the probe head, signals to and from a large number of coils on the probe head onto a reduced number of signal conductors, and by reusing coils in different measurement configurations in order to provide a higher density of inspection coverage.

21 Claims, 7 Drawing Sheets

U.S. PATENT DOCUMENTS

| | | | | |
|---|---|---|---|---|
| 4,797,250 A | | 1/1989 | Moreau | 376/293 |
| 4,808,924 A | * | 2/1989 | Cecco et al. | 324/220 |
| 4,808,927 A | * | 2/1989 | Cecco et al. | 324/220 |
| 5,001,949 A | | 3/1991 | Beneck et al. | 82/84 |
| 5,028,381 A | | 7/1991 | Duguay | 376/252 |
| 5,047,719 A | | 9/1991 | Johnson et al. | 324/242 |
| 5,049,817 A | | 9/1991 | Cecco et al. | 324/220 |
| 5,085,082 A | | 2/1992 | Cantor et al. | 73/622 |
| 5,096,656 A | | 3/1992 | Moreau | 376/245 |
| 5,117,182 A | * | 5/1992 | Cecco et al. | 324/220 |
| 5,125,272 A | | 6/1992 | Latimer et al. | 73/598 |
| 5,205,038 A | | 4/1993 | Archer et al. | 29/890.031 |
| 5,256,966 A | | 10/1993 | Edwards | 324/220 |
| 5,345,478 A | | 9/1994 | Maire et al. | 376/249 |
| 5,383,365 A | | 1/1995 | Buttram | 73/598 |
| 5,454,267 A | | 10/1995 | Moreau et al. | 73/623 |
| 5,506,503 A | * | 4/1996 | Cecco et al. | 324/220 |
| 5,526,691 A | | 6/1996 | Latimer et al. | 73/592 |
| 5,577,088 A | | 11/1996 | Senevat et al. | 376/252 |
| 5,623,203 A | * | 4/1997 | Hosohara et al. | 324/220 |
| 5,736,642 A | | 4/1998 | Yost et al. | 73/602 |
| 5,767,410 A | | 6/1998 | Lareau et al. | 73/623 |
| 5,804,963 A | * | 9/1998 | Meyer | 324/207.17 |
| 5,864,229 A | * | 1/1999 | Lund | 324/240 |

* cited by examiner

EDDY CURRENT PROBE WITH MULTI-USE COILS AND COMPACT CONFIGURATION

FIELD OF THE INVENTION

The present invention relates to non-destructive testing of conductive materials, namely eddy-current testing. More particularly, the invention relates to eddy current testing (ECT) probes, for example of the type suitable for inspecting heat exchanger tubes.

BACKGROUND OF THE INVENTION

ECT probes are well known in the art, and have various configurations depending on the nature of the material being tested. Some ECT probes are adapted for testing planar surfaces, others for testing tubes. In the case of tubes, both the interior and the exterior may be tested, and the probes are suitably adapted accordingly. ECT probes, in the case of heat exchanger tube inspection probes for inspecting the insides of heat exchanger tubes, have a probe head with coils for inducing and detecting eddy currents in the conductive material being tested. Coils may be configured in arrangements known as "bracelets" of coils, namely series of coils on the circumferential surface of the probe head. A bracelet may be provided as circumferential bands consisting of many coils.

The instrumentation for ECT consists of the probe including the probe head having the coils, signal generator and receiver equipment, the cabling connecting the probe to the signal generator and receiver equipment, and the signal analyzer equipment for analyzing the data and providing an indication of faults in the material being tested. The probe and cabling is typically subjected to extreme industrial environments which place considerable physical stress on the equipment. In the case of tube inspection, the cabling includes often a flexible shaft or tube for inserting the probe into the heat exchanger tubes, and the electrical signal conductors must therefore be durable, reliable and as thin as possible to fit inside the flexible shaft, and also to lessen the burden of cable manipulation from the signal processing equipment and the probe.

A common ECT technique to inspect tubes is to use a bobbin coil. This type of probe examines an entire cross-section of the tube at once. The difficulty is to detect small volume flaws, long axial flaws, and circumferential flaws, anywhere on either the inside or outside of the tube, and especially where the tubes are expanded.

An improved technique to the detect flaws described above is the use of probes that use one or a few small rotating coil, scanning the surface of the tube. The small coil or coils only look at a small portion of the tube surface at any given time, increasing sensitivity. Because of the mechanical rotation, such probes are typically slow.

The use of an array of coils, such as a bracelet, ensures that only small surface areas are inspected with each coil, resulting in sensitivity similar to that of the rotating probes, but without requiring mechanical rotation. Array probes, when coupled with adequate data acquisition systems provide excellent sensitivity at much greater speeds than rotating probes.

Furthermore, providing a very large number of coils in an effort to satisfy the requirement for quality of detection also results in a large number of conductors being required for carrying the coil signals. While it is possible to use smaller wires, smaller wires are more fragile, have poorer transmission characteristics, and as they are brought closer together, they have greater crosstalk.

SUMMARY OF THE INVENTION

It is an object of the present invention to provide an ECT probe which overcomes many of the drawbacks associated with known ECT probes.

More particularly, it is a first object of the present invention to provide an ECT probe which uses an arrangement of coils in different measurement configurations so as to involve coil reuse. By "coil reuse", it is meant that at least one coil from one measurement configuration is also used in another measurement configuration with at least some different coils. According to this aspect of the invention a coil may be used during one measurement as a transmit coil, and during a subsequent measurement as a receive coil. Likewise, one of two coils in a differential mode configuration during one measurement may be used in a subsequent measurement in a differential mode configuration with a different other coil, or as an absolute coil. Preferably, an array of closely arranged coils is provided and the coils are used in different measurement configurations, so as to detect faults in the surface of the material being tested in a greater number of positions (i.e. a higher density of inspection coverage), and possibly directions.

It is a second object of the present invention to provide an ECT probe which reduces the number of conductors connecting the probe coils to the instrumentation by selectively connecting coils to conductors at the probe end (or routing coil signals onto conductors). Preferably, such selective connection is done using a multiplexer switch controlled by a selection signal. Using solid state switches high selection rates are possible, and high speed scanning is possible.

Preferably, coils not being used in a measurement are disconnected or isolated using devices, such as separate solid state switches.

According to a broad aspect of the invention, there is provided a method of detecting faults in a conductive material to be tested using eddy currents, the method comprising:

a) providing a probe head having an arrangement of coils arranged on a surface of the probe to induce eddy currents in the conductive material to be tested, wherein the arrangement allows the probe to cover an area transverse to a direction of displacement of the probe head during inspection;

b) selectively exciting one of the coils with an AC source to induce an eddy current in the material;

c) measuring eddy current flow in the conductive material to be tested using at least one of said coils;

d) repeating steps b) and c) to cover the area transverse to the direction of displacement in different measurement configurations in which at least one of:

i. one of the coils used as a receiver coil is reused as a driven coil;

ii. the excited one of the coils is reused as a receiver coil;

iii. one of two or more coils used as receiver coils in a differential mode is used as a receiver coil with a different other receiver coil;

iv. a same transmit conductor is used for connecting the AC source to the probe head, step b) comprising switching the excited coil to the transmit conductor; and v. a same receiver conductor is used for connecting a receiver to the probe head, step c) comprising switching one of the at least one of the coils to the receiver conductor.

BRIEF DESCRIPTION OF THE DRAWINGS

The invention will be better understood by way of the following detailed description of a preferred embodiment with reference to the appended drawings, in which.

DETAILED DESCRIPTION OF THE PREFERRED EMBODIMENT AND OTHER EMBODIMENTS

In the preferred embodiment, a number of advantageous features provided according to the invention are combined into a single ECT probe system. In the preferred embodiment, the probe is a heat exchanger tube inspection probe, although the invention may be applied to other types of ECT probes as will be apparent to those skilled in the art.

Figure 1:
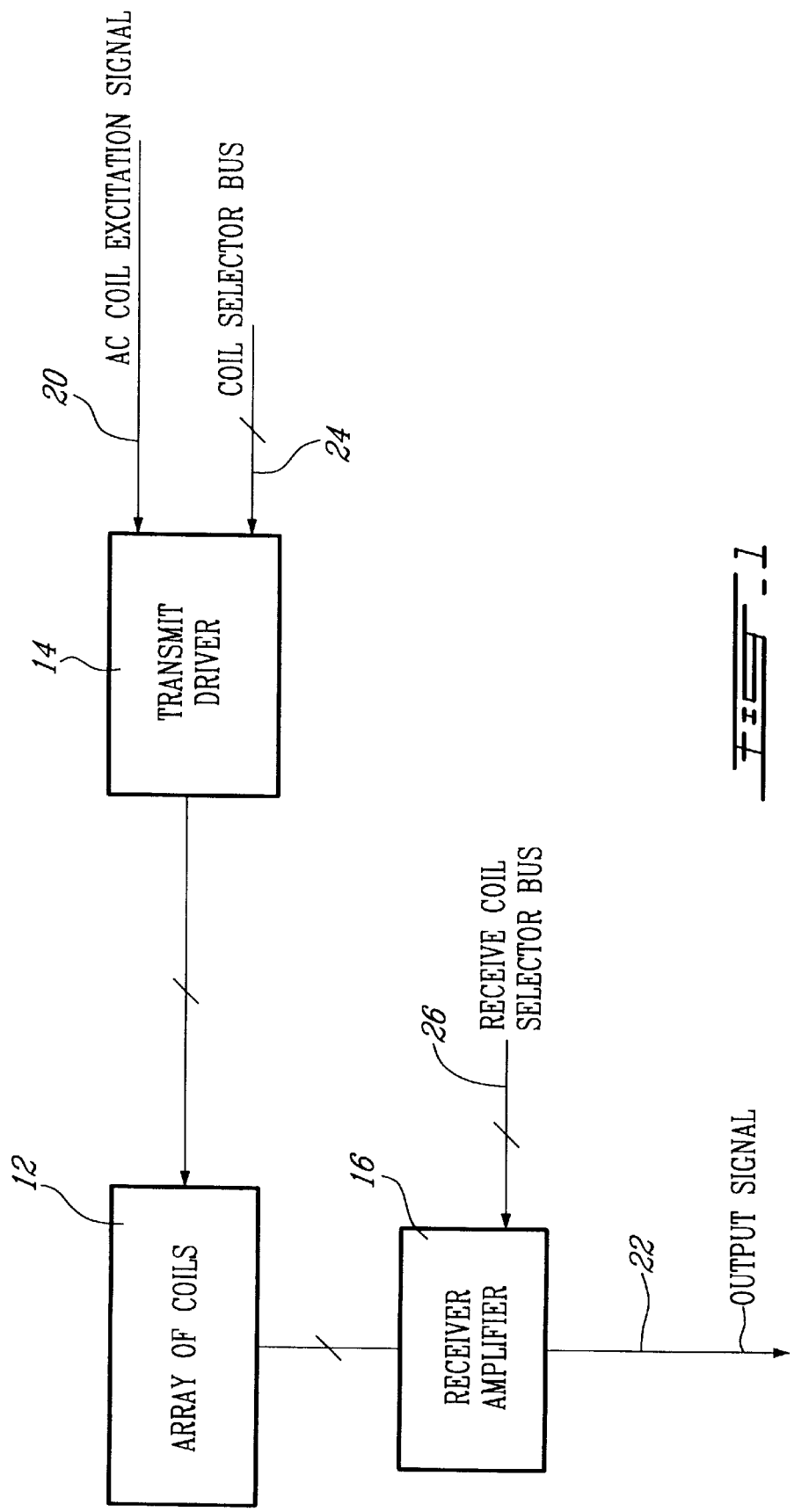
FIG. 1 is a schematic block diagram of the ECT probe system according to the preferred embodiment.

FIG. 1 illustrated a system block diagram of a probe having a configuration according to the invention. The coils are arranged according to FIG. 2 in a bracelet array having three rows of 16 coils designated by reference numeral 12. In the preferred embodiment, the coils 12 are circular coils having a central axis. The filament wires of the coils are small and the coils are mounted in the probe body such that the coils are protected against filament breakage due to shock. It will be appreciated that non-circular core windings may replace coils in certain applications without adversely affecting the induction of eddy currents in the material being tested. In the preferred embodiment, the coils are arranged parallel to the surface, i.e. their axes are perpendicular to a plane of the surface of the material. Each coil 12 can be connected to either the transmit signal conductor 20 or the receiver conductor 22 via the transmit driver multiplexer switching device 14 or the receiver signal multiplexer switching device and amplifier 16, respectively. In the preferred embodiment, the cable bus connecting the probe head to the instrumentation contains separate coax cables for conductors 20 and 22, as well as a 5V DC power line and ground, a transmit coil selector bus 24, and a receiver coil selector bus 26. These conductors are bundled into a protective harness sheath and inserted into a flexible tube shaft of the probe.

The selector buses 24 and 26 are preferably single wire serial bus wires. In the preferred embodiment, the buses 24 and 26 comprise a single toggle or pulse control wire. In the case of a serial bus, it is preferred to provide the probe head with a controller having a serial interface, thus combining buses 24 and 26 into one. When the electronics at the probe head need to be reduced to conserve space, a pulse control may be more suitable. In pulse control, the selector signal acts as a clock signal for a simple digital circuit which outputs a signal on each of the 16 coil select gate signals, sequentially one-by-one. The buses 24 and 26 may alternatively comprise multiple wires to provide a parallel bus. The parallel bus may be a static control bus in which the logic signals on the wires control the switching devices directly. The wires in buses 24 and 26 may be smaller than the signal conductors 20 and 22 since they carry logic signals or lower frequency AC signals.

Figure 2:
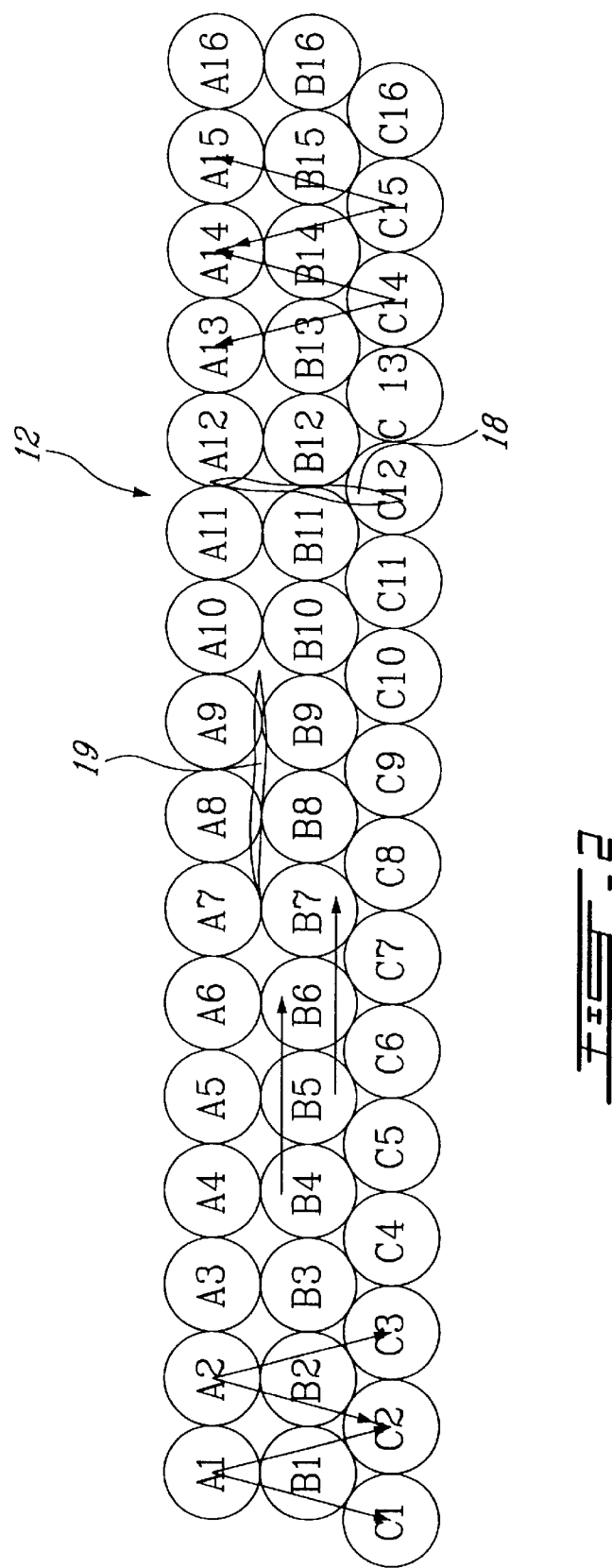
FIG. 2 is a diagram illustrating the layout of coils according to the preferred embodiment including an illustration of a first axial or longitudinal fault or crack in the surface of the material being inspected, as well as a second tangential or lateral fault or crack.

As shown in FIG. 2, some of the coils 12 function both as receiver coils and transmitter coils at different times for different measurements. The coils 12 arranged on the circumferential surface of the cylindrical probe to be substantially parallel to the surface of the conductive material being inspected. The transmit coil (or spaced apart transmit coils) induces a current in the material being tested, which current circulates in the material around the center of the transmit coil. The alternating current in the material then induces a current in nearby receiver coils. A crack or fault in the material typically causes different electrical conductivity properties, and detection of faults is possible due to this phenomenon. Current in the material passes around cracks, and consequently, it is easier to detect an elongated crack using current flowing transversely to the crack. Current directed in the direction of a narrow crack will go around the crack with little resistance. For this reason, the detection of the eddy current is done in two different directions, namely axially and circumferentially. To detect an axial crack 18, the receiver coils are selected to be circumferentially adjacent to one another, and the receiver coils are operated preferably in a differential or pseudo-differential mode. To detect a circumferential crack 19, the receiver coils are selected to be axially or longitudinally adjacent.

Figure 13:
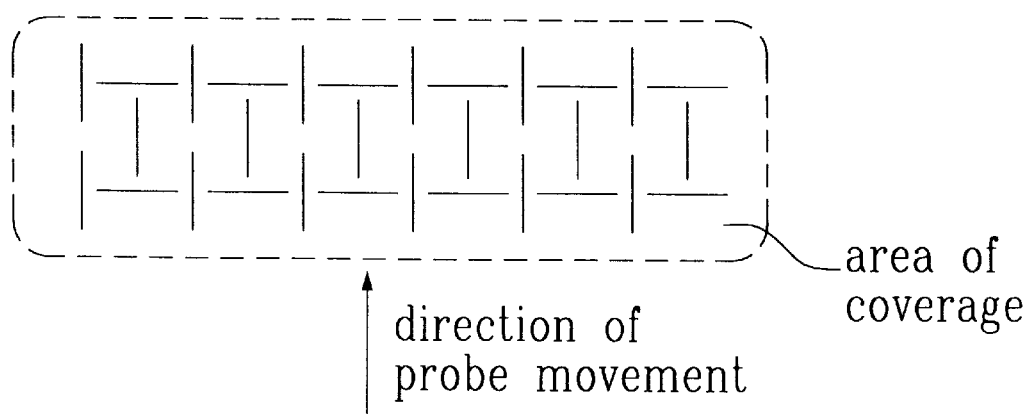
FIG. 13 is a plan view of an arrangement of coils according to an alternative embodiment.

It is also possible to provide a coil oriented with its axis parallel to the plane of the surface of the material being tested. This alternative embodiment is illustrated in FIG. 13 in plan view, in which a close arrangement of coils at right angles to one another is illustrated. The current induced in the material then flows along a segment extending adjacent the edge of the coil near the surface, and then branches out into two side lobes connecting the ends of the segment. In such a configuration, an obstruction to the current flow in the area of the segment results in a change in impedance in the coil, and the detection of the obstruction is achieved by comparing the impedance of the coil in different orientations. This can be done either by rotating the coil (not shown), or by providing coils in different fixed orientations within substantially the same region of the probe, as shown in FIG. 13. In this embodiment, elements 16 and 22 as shown in FIG. 1 are not used, and instead the instrumentation generating the transmit AC signal 20 measures the impedance of coils 12 directly.

As can be seen from FIG. 2, the choice of transmit coil and receiver coil from the matrix of coils 12 is freely selected by selector signals 22 and 24. In the preferred embodiment, the receiver coil is a single coil instead of a receiver coil pair. Therefore, the receiver coil signal is read and stored for a first of two receiver coils, and then the selector signal 24 is used to select the other of the two receive coils whose signal is read. Instead of using two differentially connected receiver coils, the invention allows each of two coils to be read separately in time, and then a pseudo-differential signal to be obtained by processing at the instrumentation. Pseudo-differential signal detection has been found to be satisfactory. Alternatively, the switching device 16 could be made to connect two coils simultaneously in differential mode to its amplifier. The number of coils switches may be doubled or may remain the same depending on the coil arrangement geometry and system flexibility. It is also possible to have separate output signals for two receiver coils, and to connect such output signals in a simultaneous differential mode at the instrumentation.

According to the invention, the instrumentation controls the coil selector signals to measure eddy currents using a particular measurement configuration for a brief period of time before electronically changing the selected coils to a new measurement configuration. All desired measurement configurations are thus employed to take measurements of the surface of the material being tested within a relatively short period of time. This period of time is sufficiently short, compared to the probe travel speed and defect sizes, so that one set of measurements are made at substantially the same axial location on the tube. Rotation of the probe head is thus not required. Both circumferential and axial cracks are detected because the measurement configurations cover both directions of receiver coils. Because the coils cover a sufficiently small area, any significant crack will not be missed. Because of the reuse of coils, a higher density of detection is provided than with conventional coil bracelet systems.

In the preferred embodiment shown in FIG. 2, the middle row contains the coils which can be driven or excited to transmit and also selectively connected to receive. The outer row A is aligned in the axial direction of the probe with row B, while row C is offset and close packed with respect to the middle row B. When row A transmits, row C receives, and vice versa, as shown by the arrows. In the mode for detecting axial cracks or faults, a driven coil from row A emits while a pair of coils in row C receive, or a driven coil from row C emits while a pair of coils in row A receive. In this arrangement, the receiver coils are spaced from the transmit coil by one coil. Likewise, in the circumferential mode, a transmit coil is selected from row B and a receiver coil is taken as the second coil over on the same row, as shown by the arrows. Of course, two receiver coils, one from each side, may be read simultaneously. Each coil in row B may be used to transmit and cover with the greatest detail the surface of the material being inspected. It will be appreciated that a differential pair of coils can also be used for detecting circumferential cracks 19, and in fact the number of coil detection configurations is very large.

In the preferred embodiment, there are multiple receive conductors 22, and more than one coil is excited to transmit at the same time. It is important that excited coils be separated by a good distance to avoid inductive influence between them. However, depending on the capacity of instrumentation to process multiple signals and the dimensions of the probe, it is desirable to excite as many non-interfering coils as possible to measure eddy currents as quickly as possible.

Figure 3:
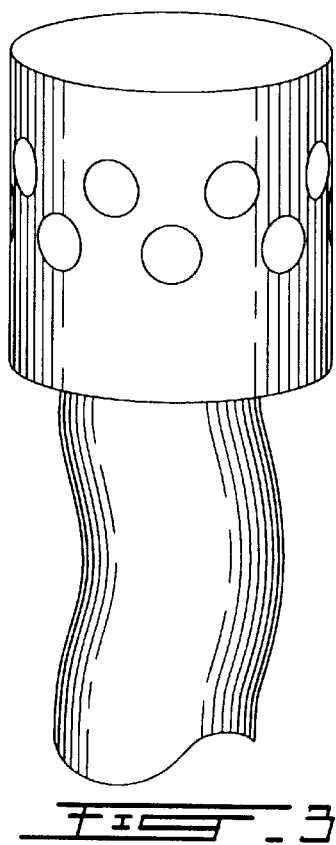
FIG. 3 is a perspective view of a probe head adapted for inspecting boiler tubes, the probe head having two rows of coils.
Figure 8:
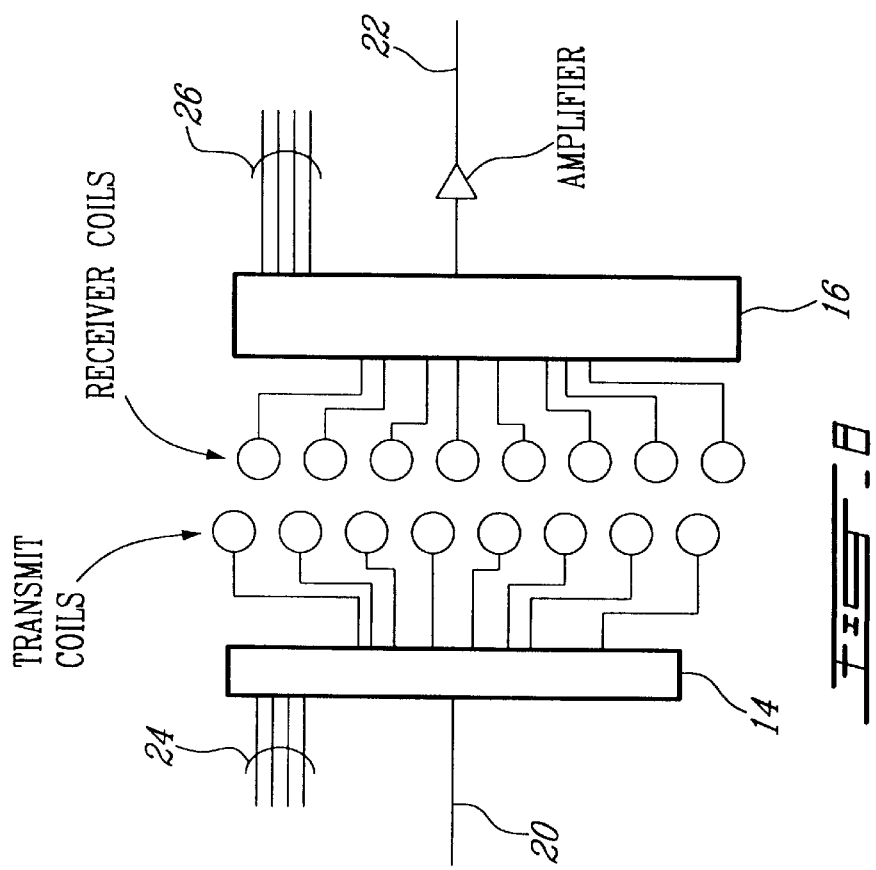
FIG. 8 is a block diagram of a switching circuit connecting transmit coils to a single transmit conductor and receiver coils to a single receiver conductor.

It will be appreciated that various probe head configurations are possible according to the present invention. In the embodiment of FIG. 3, a probe head is shown having two rows of coils wherein the second row is staggered with respect to the first row. The second row is connected by a multiplexer switch to the transmit conductor 20 only, and is thus dedicated to transmission. The first row is connected by a multiplexer switch to a single receiver conductor 22, and is thus dedicated to receiving. The circuit block diagram for this embodiment is illustrated in FIG. 8.

Figure 4:
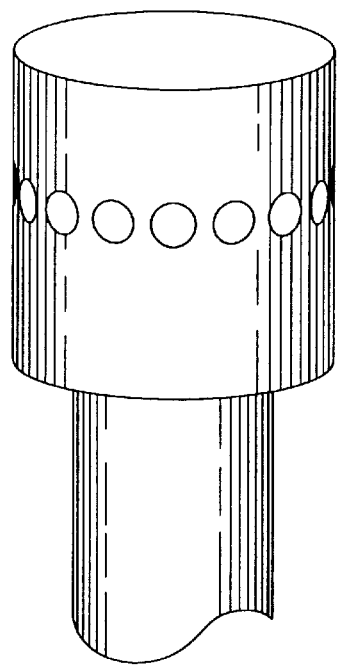
FIG. 4 is a perspective view of a probe head similar to FIG. 3, except with one row.
Figure 9:
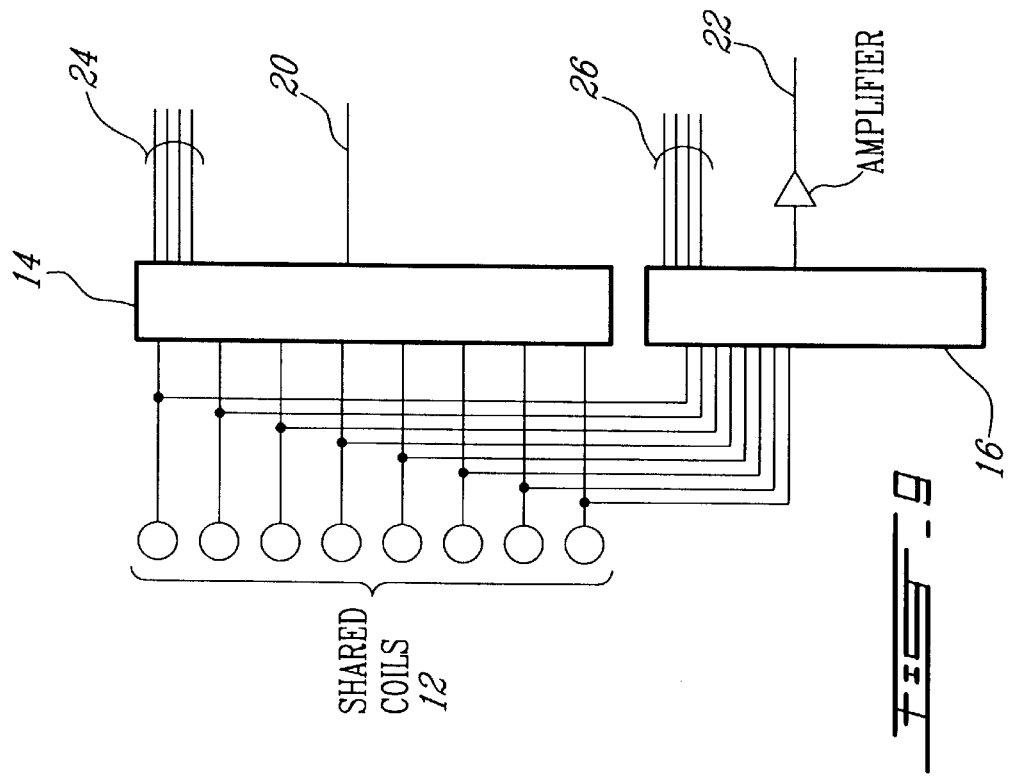
FIG. 9 is a block diagram of a switching circuit connecting a row of coils to a single transmit conductor and also to a single receive conductor.

In the embodiment of FIG. 4, a single row of coils is provided which is connected by multiplexer 14' to conductor 20 and by multiplexer 16' to conductor 22. This embodiment illustrates a simpler configuration involving both coil reuse and the use of a single conductor 20 and 22 for all coils. The circuit block diagram for this embodiment is illustrated in FIG. 9.

Figure 5:
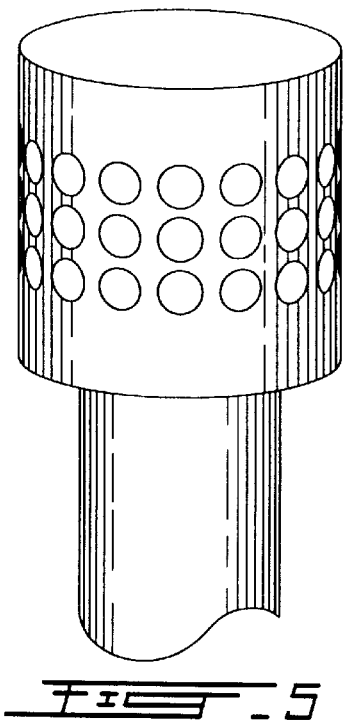
FIG. 5 is a perspective view of a probe head similar to FIG. 3, except with three rows.
Figure 10:
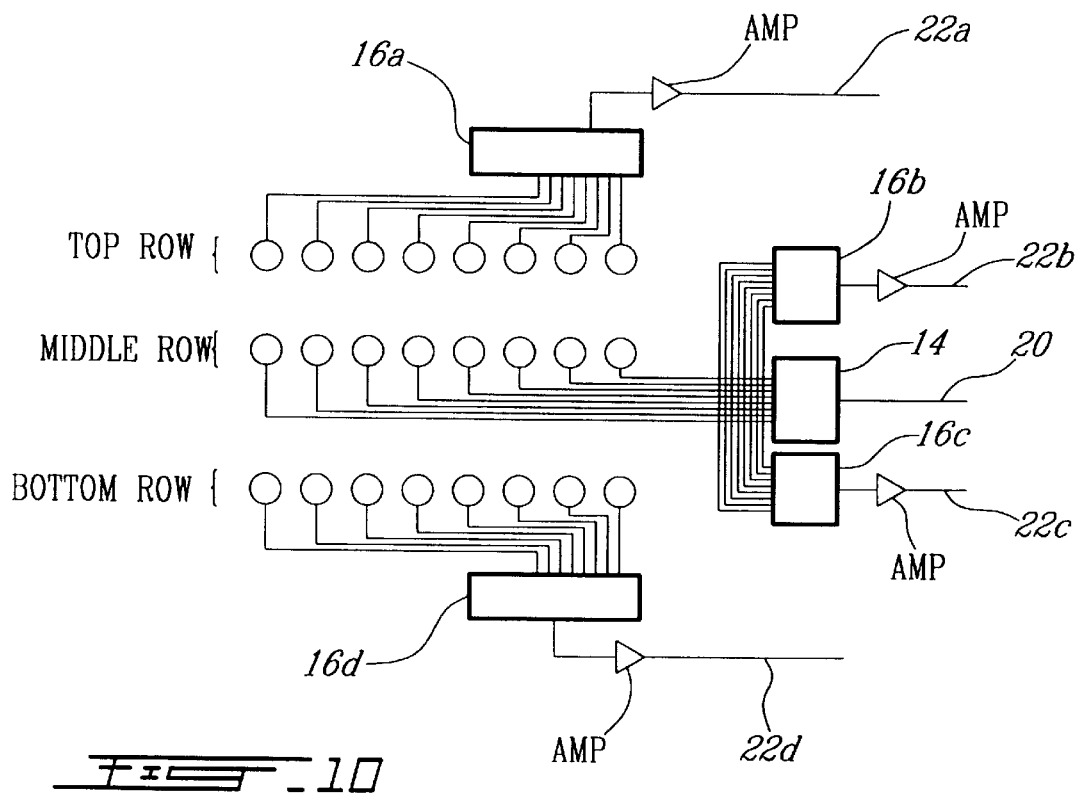
FIG. 10 is a block diagram of a switching circuit connecting a middle row of coils to a single transmit conductor and to two receive conductors, and also top and bottom rows of coils to top and bottom row receiver conductors.

The embodiment of FIG. 5 makes use of three rows of coils 12, in which the transmit multiplexer 14' is connected to the middle row, and the receiver multiplexer and amplifier 16 comprises a first multiplexer 16a for the first top row of coils, second and third multiplexers 16b and 16c for the middle row, and a fourth multiplexer 16d for the bottom row. This allows for a measurement configuration consisting of a central transmit coil surrounded by four receiver coils. Each coil in the middle row is used as the transmit coil, one after the other, to test the entire inside circumference of the tube. The circuit block diagram for this embodiment is illustrated in FIG. 10.

Figure 6:
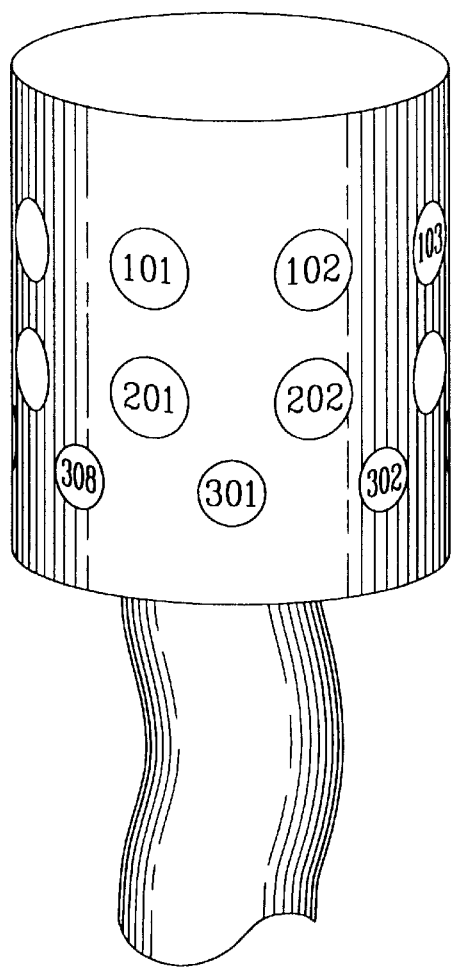
FIG. 6 is a perspective view of a probe head similar to FIG. 5, except with the last row staggered with respect to the second row.

In the embodiment of FIG. 6, the last row is staggered and is used for differential detection of axial cracks. Two receiver multiplexers are thus connected to the last row for outputting two receiver signals on conductors 22 and 22'. The transmit signal is connected to either the first or the second row of coils. In the preferred embodiment, a coil in the first row transmits while two coils in the third row receive signals for differential detection of axial cracks. This places a separation of one coil between the transmit coil and the receive coils. In the circumferential mode, the transmit coil is selected to be from the first row and subsequently from the second row, while the corresponding receiver coil is taken from the same row, again with one coil between the transmit and receiver coils.

Figure 7:
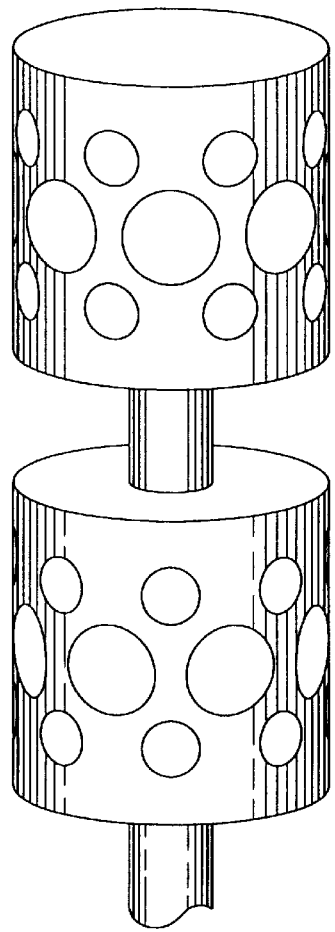
FIG. 7 is a perspective view of a probe head similar to FIG. 5, except that the middle row has larger coils than the first and third rows.

In the embodiment of FIG. 7, the middle row is reserved for transmission, and the coils in the middle row are larger than the receive coils in the top and bottom rows. For each transmit coil, there are four surrounding receiver coils, one in each corner, differential measurements can be taken between any two adjacent pairs of receiver coils. As previously described, the differential measurement can be achieved either by connecting the two coils differentially and measuring the difference signal, or by buffering or storing the signal from one coil and then subtracting the signal from the other coil by the stored signal. In this embodiment, receiver coils are reused, and thus the transmitted coils are arranged closer to one another to provide better coverage.

Figure 11:
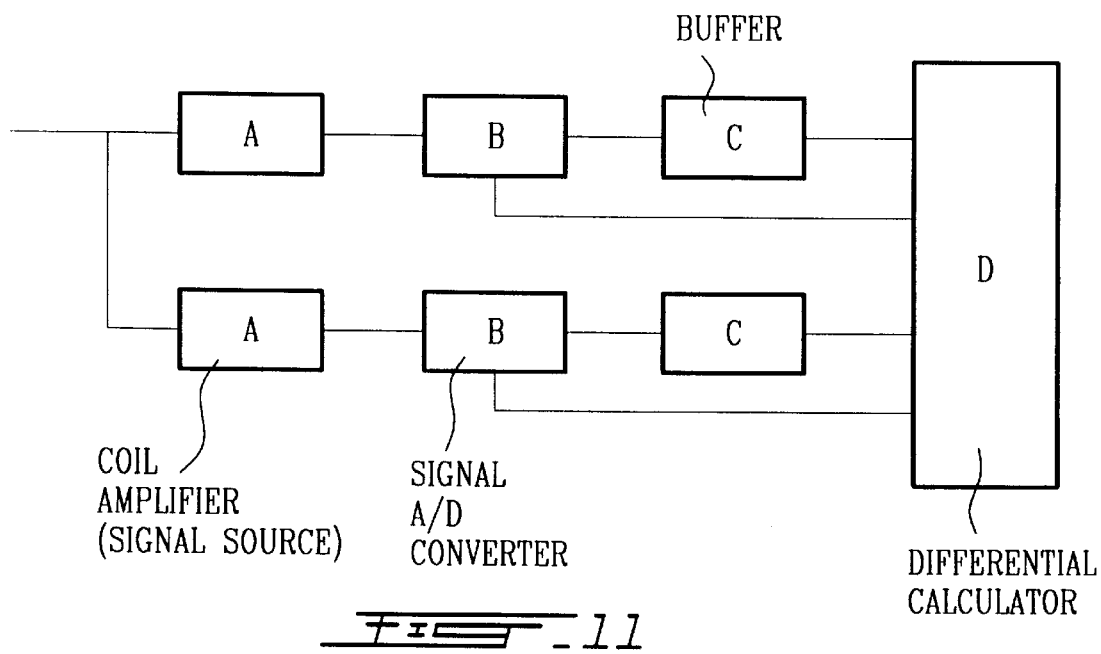
FIG. 11 is a block diagram of a signal processor computing a pseudo-differential signal from a stored receiver coil signal and a subsequently obtained receiver coil signal.
Figure 12:
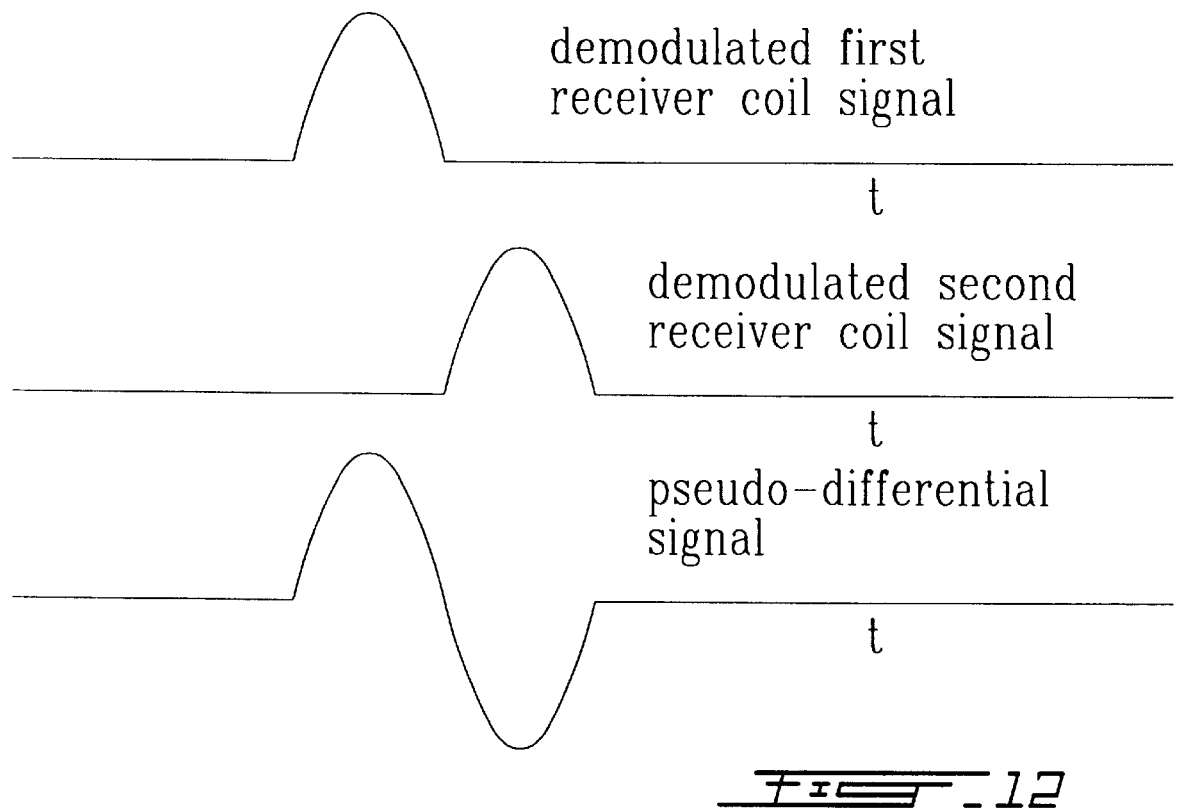
FIG. 12 is a signal diagram illustrating the transmit signal, the first stored receiver coil signal, the subsequently obtained receiver coil signal, and the calculated pseudo-differential signal.

In the embodiment of FIG. 11, a pseudo-differential mode is provided by buffering the signal from a first one of a pair of receiver coils being used in a differential configuration, and thereafter measuring the signal from a second one of the pair of receiver coils. The difference between the two signals is subtracted to obtain the pseudo-differential signal. As shown in FIG. 12, the transmit signal is a sine wave having a predetermined frequency. The first signal is buffered beginning from a predetermine phase reference with respect to the transmit signal. The second signal is likewise referenced with respect to the phase of the transmit signal, and the two receiver signals acquired one after the other are subtracted to yield the pseudo-differential signal.

It will be appreciated that many variants and alternative configurations are possible within the scope of the present invention, as defined in the appended claims.

What is claimed is:

1. A method of detecting faults in a conductive material to be tested using eddy currents, wherein the differential mode is a pseudo-differential mode, the method comprising the steps of:
   a) providing a probe head having an arrangement of coils arranged on a surface of the probe to induce eddy currents in the conductive material to be tested, wherein the arrangement allows the probe to cover an area transverse to a direction of displacement of the probe head during inspection;
   b) selectively exciting one of the coils with an AC source to induce an eddy current in the material;
   c) measuring and recording over time eddy current flow in the conductive material to be tested using at least one of said coils;
   d) repeating steps b) and c) to cover the area transverse to the direction of displacement in different measurement configurations in which at least one of alternatives i, ii, iii, iv, and v is used:
      i. one of the coils used as a receiver coil is reused as a driven coil;
      ii. the excited one of the coils is reused as a receiver coil;
      iii. one of two or more coils used as receiver coils in a differential mode is used as a receiver coil with a different other receiver coil;
      iv. a same transmit conductor is used for connecting the AC source to the probe head, wherein said step b) further comprises switching the excited coil to the transmit conductor; and
      v. a same receiver conductor is used for connecting a receiver to the probe head, wherein said step c) further comprises switching one of the at least one of the coils to the receiver conductor; and
   e) subtracting the measurement of eddy current flow of two of said receiver coils to obtain a pseudo-differential measurement from the two receiver coils.

2. The method as claimed in claim 1, wherein the probe head comprises a transmit multiplexer switch for connecting the excited coil to the transmit conductor, and said step b) further comprises transmitting a selector signal to the transmit multiplexer switch.

3. The method as claimed in claim 1, wherein the coils are arranged to be substantially parallel to a surface of the material to be tested, and said eddy current induced by the excited coil in the material to be tested is measured by at least one receiver coil, the probe head comprising a receiver multiplexer switch for connecting one of the at least one receiver coil to the receiver conductor, and said step c) comprises transmitting a selector signal to the receiver multiplexer switch.

4. The method as claimed in claim 3, wherein only one receiver conductor is provided, and said step c) is carried out twice to obtain sequentially the measurement of eddy current flow in the conductive material to be tested between the excited one of the coils and each of two receiver coils.

5. The method as claimed in claim 3, wherein said step c) comprises amplifying at the probe head a signal from the one of the at least one receiver coil after the receiver multiplexer switch.

6. The method as claimed in claim 3, wherein the selector signal is a toggle signal causing the receive multiplexer switch to connect to a next coil in a series of the arrangement of coils.

7. The method as claimed in claim 1, wherein the coils are arranged in planes perpendicular to a surface of the material to be tested, and said step (c) comprises measuring an impedance of the same excited coil.

8. The method as claimed in claim 1, wherein the probe head is cylindrically shaped and adapted to be inserted into a heat exchanger tube.

9. The method as claimed in claim 8, wherein the coils are arranged to be substantially parallel to a surface of the material to be tested, and in said step c) the eddy current induced by the excited coil in the material to be tested is measured by at least one receiver coil, and the arrangement of coils comprises at least two circumferential bracelets of coils arranged in rows.

10. The method as claimed in claim 9, wherein rapid switching of connections of the driven and the receiver coils is carried out to obtain a large number of the measurements of the eddy current flow within a short period of time during which the probe head moves little, such that a scanning of the conductive surface where the coils are located takes place.

11. The method as claimed in claim 10, wherein both axial and circumferential measurement configurations are used.

12. A method of detecting faults in a conductive material to be tested using eddy currents, the method comprising the steps of:
   a) providing a probe head having an arrangement of coils arranged on a surface of the probe to induce eddy currents in the conductive material to be tested, wherein the arrangement allows the probe to cover an area transverse to a direction of displacement of the probe head during inspection;
   b) selectively exciting one of the coils with an AC source to induce an eddy current in the material, wherein coils excited to transmit are separated from receiver coils by one coil not used in the present measurement of the eddy current flow;
   c) measuring eddy current flow in the conductive material to be tested using at least one of said coils;
   d) repeating steps b) and c) to cover the area transverse to the direction of displacement in different measurement configurations in which at least one of alternatives i, ii, iii, iv, and v is used:
      i. one of the coils used as a receiver coil is reused as a driven coil;
      ii. the excited one of the coils is reused as a receiver coil;
      iii. one of two or more coils used as receiver coils in a differential mode is used as a receiver coil with a different other receiver coil;
      iv. a same transmit conductor is used for connecting the AC source to the probe head, wherein said step b) further comprises switching the excited coil to the transmit conductor; and v. a same receiver conductor is used for connecting a receiver to the probe head, wherein said step c) further comprises switching one of the at least one of the coils to the receiver conductor.

13. The method as claimed in claim 12, wherein three rows of the bracelets of coils are provided, said three rows consisting of a top, middle, and bottom row, wherein in a first mode, a coil from each of said top and bottom rows are used as receiver coils while a coil from said middle coil is used as a transmit coil, and in a second mode, a coil from one of said top and bottom rows is used as a transmit coil while at least one coil from another of said top and bottom rows is used as a receive coil.

14. The method as claimed in claim 13, wherein rapid switching of connections of the driven and the receiver coils is carried out to obtain a large number of the measurements of the eddy current flow within a short period of time during which the probe head moves little, such that a scanning of the conductive surface where the coils are located takes place.

15. The method as claimed in claim 13, wherein both axial and circumferential measurement configurations are used.

16. The method as claimed in claim 12, wherein the probe head comprises a transmit multiplexer switch for connecting the excited coil to the transmit conductor, and said step b) further comprises transmitting a selector signal to the transmit multiplexer switch.

17. The method as claimed in claim 12, wherein the coils are arranged to be substantially parallel to a surface of the material to be tested, and said eddy current induced by the excited coil in the material to be tested is measured by at least one receiver coil, the probe head comprising a receiver multiplexer switch for connecting one of the at least one receiver coil to the receiver conductor, and said step c) comprises transmitting a selector signal to the receiver multiplexer switch.

18. The method as claimed in claim 12, wherein rapid switching of connections of the driven and the receiver coils is carried out to obtain a large number of the measurements of the eddy current flow within a short period of time during which the probe head moves little, such that a scanning of the conductive surface where the coils are located takes place.

19. The method as claimed in claim 12, wherein both axial and circumferential measurement configurations are used.

20. The method as claimed in claim 12, wherein coils excited to transmit are separated from receiver coils by one coil not used in the present measurement of the eddy current flow.

21. The method as claimed in claim 20, wherein said arrangement of coils comprises at least one circumferential bracelet of coils arranged in a row.

\* \* \* \* \*